(12) United States Patent
Hofrichter

(10) Patent No.: US 11,953,632 B2
(45) Date of Patent: Apr. 9, 2024

(54) X-RAY DETECTOR COMPONENT, X-RAY DETECTION MODULE, IMAGING DEVICE AND METHOD FOR MANUFACTURING AN X-RAY DETECTOR COMPONENT

(71) Applicant: ams International AG, Jona (CH)

(72) Inventor: Jens Hofrichter, Jona (CH)

(73) Assignee: AMS INTERNATIONAL AG, Jona (CH)

( * ) Notice: Subject to any disclaimer, the term of this patent is extended or adjusted under 35 U.S.C. 154(b) by 156 days.

(21) Appl. No.: 17/428,131

(22) PCT Filed: Jan. 24, 2020

(86) PCT No.: PCT/EP2020/051811
§ 371 (c)(1),
(2) Date: Aug. 3, 2021

(87) PCT Pub. No.: WO2020/160940
PCT Pub. Date: Aug. 13, 2020

(65) Prior Publication Data
US 2022/0128718 A1    Apr. 28, 2022

(30) Foreign Application Priority Data
Feb. 4, 2019 (EP) .................................... 19155294

(51) Int. Cl.
*G01T 1/24* (2006.01)
*A61B 6/00* (2006.01)
(Continued)

(52) U.S. Cl.
CPC ............ *G01T 1/247* (2013.01); *A61B 6/4233* (2013.01); *G01N 23/083* (2013.01); *G01N 23/10* (2013.01);
(Continued)

(58) Field of Classification Search
CPC .... A61B 6/4233; G01N 23/083; G01N 23/10; G01N 23/18; G01T 1/241; G01T 1/247;
(Continued)

(56) References Cited

U.S. PATENT DOCUMENTS 5,159,419 A * 10/1992 Hosack ............. H01L 27/14831
257/446
5,528,043 A * 6/1996 Spivey .............. H01L 27/14658
250/580

(Continued)

FOREIGN PATENT DOCUMENTS

| EP | 3734652 A1 | 11/2020 |
| KR | 1999-0064216 A | 7/1999 |
| WO | 02063339 A1 | 8/2002 |

OTHER PUBLICATIONS

Garcia-Sciveres, M. and Wermes, N., "A review of advances in pixel detectors for experiments with high rate and radiation", 2018, Rep. Prog. Phys. 81, 066101, 43pp (Year: 2018).*

(Continued)

*Primary Examiner* — Blake C Riddick
(74) *Attorney, Agent, or Firm* — MH2 TECHNOLOGY LAW GROUP LLP

(57) ABSTRACT

The invention relates to an X-ray detector component comprising an X-ray detector chip made from a silicon substrate and comprising charge collecting electrodes. The X-ray detector chip is suitable for providing an X-ray-dependent current at the charge collecting electrodes. The X-ray detector component further comprises a CMOS read-out circuit chip comprising connection electrodes. The X-ray detector chip and the CMOS read-out circuit chip are mechanically and electrically connected in such a manner that the charge collecting electrodes and the connection electrodes are electrically connected. The invention further relates to an X-ray (Continued)

detection module, an imaging device and a method for manufacturing an X-ray detector component.

20 Claims, 5 Drawing Sheets

(51) Int. Cl.
    *A61B 6/42*         (2024.01)
    *G01N 23/083*     (2018.01)
    *G01N 23/10*      (2018.01)
    *G01N 23/18*      (2018.01)
    *H01L 27/146*     (2006.01)

(52) U.S. Cl.
    CPC ............ *G01N 23/18* (2013.01); *G01T 1/241* (2013.01); *G01T 1/248* (2013.01); *H01L 27/14661* (2013.01); *H01L 27/1469* (2013.01)

(58) Field of Classification Search
    CPC ............ G01T 1/248; H01L 27/14661; H01L 27/1469
    See application file for complete search history.

(56) References Cited

U.S. PATENT DOCUMENTS

| | | | |
|---|---|---|---|
| 5,677,539 A | 10/1997 | Apotovsky et al. | |
| 5,886,353 A * | 3/1999 | Spivey | H04N 5/32 250/580 |
| 6,107,619 A * | 8/2000 | Cunningham | H01L 27/14634 257/463 |
| 6,188,089 B1 * | 2/2001 | Spartiotis | H01L 27/14618 257/632 |
| 6,323,475 B1 * | 11/2001 | Spartiotis | H01L 27/14658 250/214 R |
| 6,703,617 B1 * | 3/2004 | Spartiotis | G01T 1/243 257/E27.146 |
| 2004/0251420 A1 | 12/2004 | Sun | |
| 2005/0167606 A1 * | 8/2005 | Harrison | G01T 1/241 250/395 |
| 2008/0258072 A1 * | 10/2008 | Junno | H01L 27/14659 250/389 |
| 2009/0045346 A1 * | 2/2009 | Von Kanel | H01L 27/14689 250/370.09 |
| 2009/0096046 A1 * | 4/2009 | Heringa | H01L 27/14663 257/428 |
| 2009/0200478 A1 * | 8/2009 | Bethke | G01T 1/247 250/370.08 |
| 2009/0290680 A1 * | 11/2009 | Tumer | G01T 1/247 250/311 |
| 2010/0014631 A1 * | 1/2010 | Sonsky | G01T 1/2018 250/361 R |
| 2010/0106296 A1 * | 4/2010 | Chou | G06N 3/008 700/245 |
| 2010/0127314 A1 * | 5/2010 | Frach | H01L 31/1804 257/292 |
| 2014/0210035 A1 * | 7/2014 | Park | G01T 1/208 257/458 |
| 2015/0060676 A1 * | 3/2015 | Couture | H01L 27/14636 250/361 R |
| 2015/0279890 A1 * | 10/2015 | Spartiotis | H01L 27/14636 257/428 |
| 2016/0015339 A1 * | 1/2016 | Danzer | H01L 27/14661 250/394 |
| 2016/0141318 A1 * | 5/2016 | Arendonk | H04N 5/32 250/370.09 |
| 2017/0055923 A1 * | 3/2017 | Meylan | A61B 6/032 |
| 2017/0194374 A1 * | 7/2017 | Jacob | H01L 27/14689 |
| 2017/0194375 A1 * | 7/2017 | Jacob | H01L 27/14663 |
| 2017/0373110 A1 | 12/2017 | Von Känel | |
| 2018/0156927 A1 | 6/2018 | Cao et al. | |
| 2018/0192977 A1 * | 7/2018 | Jin | A61B 6/032 |
| 2018/0240842 A1 * | 8/2018 | Meylan | A61B 6/032 |
| 2019/0172860 A1 * | 6/2019 | Von Känel | H01L 27/14643 |
| 2019/0227182 A1 * | 7/2019 | Ergler | G01T 7/00 |
| 2019/0280042 A1 * | 9/2019 | Von Känel | H01J 49/025 |
| 2019/0288026 A1 * | 9/2019 | Von Kaenel | H01L 31/1844 |
| 2020/0209415 A1 * | 7/2020 | Veale | G01T 1/241 |
| 2020/0335485 A1 * | 10/2020 | Cao | G01N 23/046 |
| 2021/0011180 A1 * | 1/2021 | Yamada | H01L 31/0224 |
| 2021/0382188 A1 * | 12/2021 | Steadman Booker | G01T 1/17 |

OTHER PUBLICATIONS

Deptuch, G. et al., "Fully 3-D Integrated Pixel Detectors for X-Rays", IEEE Transactions on Electron Devices, vol. 63, No. 1; Jan. 1, 2016; pp. 205-214.

Zou, Y. et al., "Backside illuminated wafer-to-wafer bonding Single Photon Avalanche Diode array", IEEE, 2014, 4 pages.

International Search Report and Written Opinion in corresponding International Application No. PCT/EP2020/051811 dated Apr. 23, 2020, 11 pages.

Korean Examination Report dated Aug. 19, 2023, issued in Korean Patent Application No. 10-2021-7026870, with English translation, 11 pages.

First Chinese Office Action issued in corresponding Chinese Patent Application No. 2020800123490 dated Jan. 22, 2024, with English translation, 15 pages.

\* cited by examiner

X-RAY DETECTOR COMPONENT, X-RAY DETECTION MODULE, IMAGING DEVICE AND METHOD FOR MANUFACTURING AN X-RAY DETECTOR COMPONENT

CROSS-REFERENCE TO RELATED APPLICATIONS

The present application is the national stage entry of International Patent Application No. PCT/EP2020/051811, filed on Jan. 24, 2020, and published as WO 2020/160940 A1 on Aug. 13, 2020, which claims the benefit of priority of European Patent Application No. 19155294.2, filed on Feb. 4, 2019, all of which are incorporated by reference herein in their entirety.

FIELD OF THE INVENTION

The invention relates to an X-ray detector component, an X-ray detection module, an imaging device comprising a plurality of X-ray detector components and a method for manufacturing an X-ray detector component.

BACKGROUND OF THE INVENTION

Imaging systems based on ionizing radiation, in particular X-ray radiation, may be used in the field of medicine as well as screening and inspection of objects, e.g., material failure analysis or baggage scanning or packet scanning. Mammography systems are one form of medical imaging systems.

Mammography is a radiological procedure for screening and diagnosis of the female human breast, but also of the male and transgender human breast. Mammography is a medical imaging method using low-energy X-rays to examine the human breast.

Conventional mammography systems employ either scintillator based systems, where X-ray quants, which may be also called (X-ray) photons, are transferred to light and then later detected by photodiodes, or with direct detection systems using energy integrating detectors, where the energy is directly converted into a current.

Conventional mammography detectors are based on the following operating principles:

One approach includes detection of X-ray radiation through a phosphorescent screen, which is read out through a laser beam later on. This approach is outdated and cannot be integrated.

Another approach involves a detector using a scintillator, which transfers X-ray radiation to light and which is arranged on amorphous silicon and may be read out by thin film transistors. FIG. 1 shows an embodiment of such a detector component comprising a scintillator 2 that is arranged on an amorphous silicon (a-Si) detector 4. Thin-film transistors 6 made of amorphous silicon (a-Si) form a read-out circuit 7 on a glass substrate 8 which allows reading out signals captured with charge collecting electrodes 10 arranged at the bottom of the scintillator 2.

The scintillator 2 is made of a material that exhibits luminescence when excited by ionizing radiation. After transferring X-ray radiation 12 into light 14, the charge collecting electrodes 10 provide a current depending on the light photons. The current may be detected by the read-out circuit 7.

A third approach concerns a detector using direct detection. X-ray radiation is transferred to a current by the photoelectric effect. The current is read out through thin-film transistors. FIG. 2 shows an embodiment of such a detector component comprising a sensor element comprising a wafer-based amorphous selenium element 16 having bottom electrodes serving as charge collecting electrodes 10. A top electrode 18 is arranged on the top of the selenium element 16. A read-out circuit 7 comprising thin film transistors 6 and connection electrodes 20 is arranged on a glass substrate 8. The selenium element 16 is attached to the read-out circuit 7 in such a manner that the connection electrodes 20 and the charge collecting electrodes 10 are electrically connected. X-ray radiation 12 is detected by a direct conversion of the X-ray photons to an electrical charge captured with the charge collecting electrodes 10 and provided to the read-out circuit 7.

The three approaches mentioned above have the disadvantage that they are relatively slow with regard to the read-out speed (which is in the range of several microseconds) and thus they can only be used for integrating detectors. This means that the X-ray energy is absorbed and detected as a "grey" value.

Document US 20170373110 A1 shows a monolithic CMOS integrated pixel detector and system including X-ray detectors and methods for detection and imaging. The X-ray detector is based on a detector implementation on a CMOS chip. SiGe or Ge crystals are grown on a backside of the CMOS chip.

Document US 20040251420 A1 shows an X-ray detector with grid structured scintillators, which is a scintillator-based mammography detector. X-ray quants are transformed to light in an intermediate state. Thus, the impinging X-ray energy cannot be quantified.

This disclosure provides an improved X-ray detector component with the capability of energy resolution at low cost.

SUMMARY OF THE INVENTION

An X-ray detection module comprises a plurality of such X-ray detector components. The X-ray detection module may be comprised by an imaging device. A method relates to manufacturing of such an X-ray detector component.

The X-ray detector component comprises an X-ray detector chip comprising charge collecting electrodes; the X-ray detector chip being suitable for providing an X-ray-dependent current at the charge collecting electrodes and a CMOS read-out circuit chip comprising connection electrodes, wherein the X-ray detector chip and the CMOS read-out circuit chip are mechanically and electrically connected in such a manner that the charge collecting electrodes and the connection electrodes are electrically connected.

The X-ray detector component may be manufactured by the following method:
  providing an X-ray detector wafer comprising a plurality of charge collecting electrodes,
  providing a CMOS read-out circuit wafer comprising a plurality of connection electrodes,
  mechanically and electrically connecting the X-ray detector wafer and the CMOS read-out circuit wafer in such a manner that the charge collecting electrodes and the connection electrodes are electrically connected,
  separating the X-ray detector wafer and CMOS read-out circuit wafer, which are connected, into a plurality of X-ray detector components.

In one embodiment, the X-ray detector chip is the made from a silicon substrate.

In an alternative embodiment, the X-ray detector chip and the CMOS read-out circuit chip are connected by at least one hybrid bond. Nevertheless, hybrid bonding and making the X-ray detector chip from a silicon substrate may be combined in a same embodiment.

The X-ray detector component may be comprised by an imaging medical device for mammography which may be used for breast cancer screening, which enables detection of an early stage of breast cancer. But it provides a certain amount of false-positive findings. The X-ray detector component allows the amount of false-positive findings during breast cancer screening to be reduced.

The X-ray detector component allows energy resolved mammography. In analogy to photography, the invention seeks to improve mammography from grayscale to color. Spectrally resolving the X-ray quants onto the detector allows to distinguish between different parts of the body, such as bones, normal tissue, and cancer tissue, visible through the accumulation of contrast agents.

The invention enables energy-resolved mammography at only slightly increased costs compared to conventional devices. Compared to photon counting computer tomography systems, the costs are substantially reduced through the use of an all-silicon approach. No toxic materials such as CdTe or CdZnTe, etc., which are used in conventional devices, need to be used in this approach.

Fabricating a energy-resolved mammography detector component would result in much less false-positive findings compared to conventional devices and thus enables the diagnostic accuracy of breast cancer screening to be improved.

The X-ray detector component may use a photon counting system, which may be used for high-end computed tomography systems in combination with a silicon single-photon detector chip. The silicon detector chip has the advantage that it can be produced in a CMOS environment on a large scale, and is therefore relatively inexpensive. In combination with the tightly integrated CMOS read-out chip its absorption is sufficient for typical X-ray energies used in mammography ranging from 25 to 35 keV.

The X-ray detector component made from a silicon substrate differs from conventional X-ray detector components using very expensive materials such as CdTe or CdZnTe or the like. Those elements are toxic, carcinogenic and hazardous and should not be used wherever possible. Moreover, to date it is not possible to fabricate large substrates, such as 8" or larger. However, their stopping power is required for computed tomography systems, where X-ray energies of up to 150 keV are used. The conventional photon counting systems resort to heterogeneous integration of a highly absorbing material with a CMOS read-out chip. In contrast, in mammography only energies up to 35 keV are used, which allows the use of silicon detectors fabricated at wafer scale. Then, this would allow processing of the X-ray detector wafer and the CMOS read-out circuit wafer in a CMOS foundry at moderate to low costs.

In principle, silicon detectors could also be used with the existing thin-film transistor read-out schemes, but their speed and performance is inferior for use within a photon counting system, where high speed is mandatory and only offered by scaled CMOS nodes and circuits fabricated therein. In principle, also amorphous selenium detectors could be combined with scaled CMOS read-out circuits, however, it is doubtful whether their price would be competitive.

In one embodiment the X-ray detector component comprises a plurality of detector elements. Each detector element corresponds to a pixel and allows detecting X-ray intensity incoming to the pixel's area Hybrid bonding for connecting the X-ray detector chip and the CMOS read-out chip allows manufacturing compact X-ray detector components which differ from conventional photon counting systems resorting to heterogeneous integration of a highly absorbing material with a CMOS read-out circuit chip. Contrary to this, conventional devices use materials with a high atomic number (z-Number) that are connected to a scaled CMOS read-out integrated circuit through solder balls or stud bumps.

However, in one embodiment the X-ray detector chip and the CMOS read-out circuit chip are connected by solder means, e.g., solder balls or stud bumps, which is a proven and cost-effective joining technique.

In one embodiment, the X-ray detector chip comprises a direct X-ray detector, which directly converts X-ray photons to electrical charge and thus allows a digital image to be generated. The plurality of detector elements may be embodied as a plurality of direct X-ray detector elements.

In one embodiment, the X-ray detector chip comprises a single-photon detector, preferably a single-photon avalanche photodiode, which allows detecting a single event caused by X-ray radiation. Such an X-ray detector chip has a high sensitivity. Evaluation may be achieved by means of the CMOS read-out circuit chip comprising a photon counter circuit.

The X-ray detector components seeks to integrate a wafer-based silicon X-ray detector chip outputting a single-photon signal to an underlying wafer-based CMOS read-out circuit chip, which comprises a counting circuit. With this apparatus, it is possible to detect X-ray radiation used for mammography in the range from 25 keV up to 35 keV with a reasonable detective quantum efficiency.

In one embodiment, the charge collecting electrodes are formed in such a manner that field lines between a top electrode of the X-ray detector chip and the charge collecting electrodes are curved towards the charge collecting electrodes. The curved field lines shape the path of the electrons and focuses the electrons to the charge collecting electrodes which avoids cross-talking effects.

The same effect may be achieved by trenches, preferably filled with a non-conducting material, extending between the charge collecting electrodes.

A plurality of X-ray detector components may be provided in an X-ray detection module. Such a flat panel detection module may be placed in an image receptor of an imaging device. The imaging device may be an imaging medical device, e.g. for mammography or dental X-raying, or a screening device, e.g. for material failure analysis or baggage scanning or packet scanning.

BRIEF DESCRIPTION OF THE DRAWINGS

Non-limiting, exemplary embodiments of the invention will now be described with reference to the accompanying drawings, in which.

DETAILED DESCRIPTION

Figure 1:
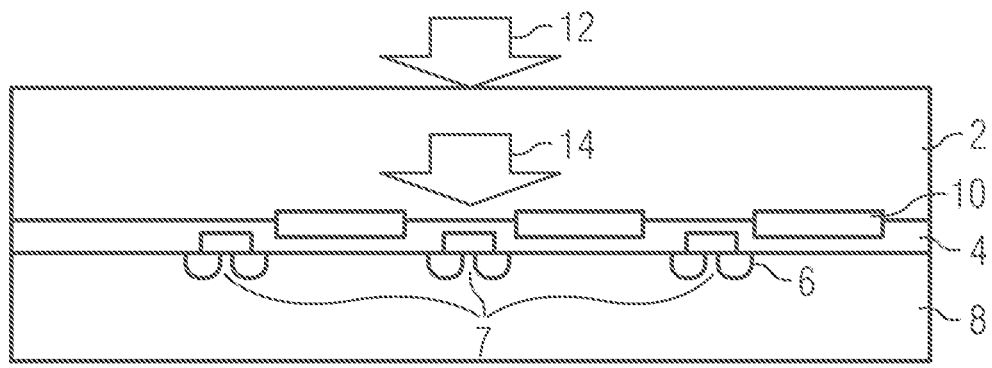
FIG. 1 shows a conventional X-ray detector component employing indirect detection using a scintillator.
Figure 2:
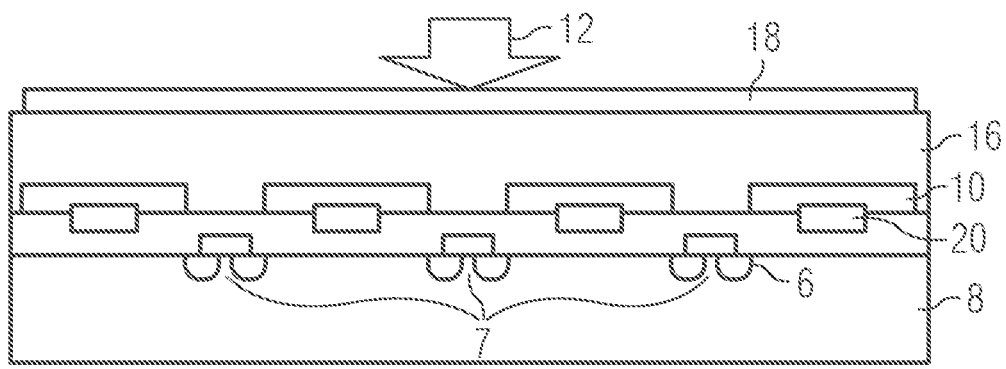
FIG. 2 shows a further conventional X-ray detector component employing direct detection.

The X-ray detector component 1 comprises an X-ray detector chip 22 serving as a sensor. The X-ray detector chip 22 having top and bottom sides comprises bottom electrodes arranged on the bottom side and serving as charge collecting electrodes 10. A top electrode 18 is arranged on the top side facing towards incoming X-rays 12. The X-ray detector chip 22 comprises a wafer-based sensor substrate 21, which is formed by separating a wafer during a manufacturing process described later. The X-ray detector chip 22 comprises a plurality of detector elements 23, each suitable for detecting the X-ray intensity of one pixel.

The sensor substrate 21 of the X-ray detector chip 22 is made from silicon and comprises at least one single-photon detector being an embodiment of a detector element 23. Usually, a plurality of single-photon detectors is arranged in an array, which has rows and columns, on the X-ray detector chip 22. Typically, the single-photon detectors in silicon are referred to as single-photon avalanche detectors (SPADs).

In principle, alternatively, the X-ray detector chip formed from a sensor wafer could be made of gallium arsenide (GaAs), which would be also available in large substrate sizes, such as 8". This would have the benefit that the GaAs wafer could be made much thinner for the same absorption, but at the expense of non-CMOS compatibility and at higher cost.

The top electrode 18 on top of the sensor substrate 21 is connected to a high (static) potential in order to deplete the sensor substrate 21. In a preferred embodiment, the sensor substrate 21 is fully depleted.

A CMOS read-out circuit chip 24 is attached to the X-ray detector chip 22 and comprises a read-out circuit 7 which comprises at least one photon counter circuit 26 including several transistors 6. The at least one counter circuit 26 is designed to count events occurring in at least one detector element 23 of the sensing X-ray detector chip 22. The scaled CMOS read-out circuit 7 is required for forming a counting system that is fast enough to capture the counts of the detector elements 23.

Usually, a plurality of counter circuits 26 are arranged in an array on the CMOS read-out circuit chip 24. A back end of line (BEOL) 27 of the CMOS read out circuit chip 24, where the transistors 6 get interconnected with wiring, faces towards the bottom side of the X-ray detector chip 22. The back end of line (BEOL) 27 that defines a front side of the CMOS read-out circuit chip 24 includes connection electrodes 20 for applying an X-ray dependent current as counter circuit inputs.

The X-ray detector chip 22 is integrated on the front side of the CMOS read-out circuit chip 24. The X-ray detector chip 22 is mechanically connected, e.g. bonded, to the CMOS read out circuit chip 24 so that the connection electrodes 20 and the charge collecting electrodes 10 are electrically connected, which is achieved by hybrid bonding in this embodiment. Hybrid bonding allows to stack and electrically connect chips of different types by bringing their flat surfaces into contact, thereby forming a connection. The CMOS read-out circuit chip 24 is scaled so that the surface area of the X-ray detector chip 22 corresponds to the surface area of the CMOS read-out circuit chip 24.

Through a cross-section (technically a SEM-EDX image would be sufficient), the silicon detector layer as well as the scaled CMOS read-out circuit 7 could be detected.

The charge collecting electrodes 10 are arranged on the connection electrodes 20. A contour line of the surface area of one of the charge collecting electrodes 10 may correspond to a contour line of the surface area of one of the connection electrodes 20. In other words, their surface areas have the same size and form. Alternatively, the contour line of the surface area of one of the charge collecting electrodes 10 may lie within or outside the contour line of the surface area of one of the connection electrodes 20. In the embodiment shown in FIG. 3, the charge collecting electrodes 10 are larger than and overlap the connection electrodes 20.

A photon counter detector is formed by connecting one single-photon detector to one counter circuit 26 which may be achieved by connecting the respective charge collecting electrode 10 and the connection electrode 20. Each photon counter detector makes up an individual pixel containing information about X-ray intensity incoming to the pixel's area. The X-ray detector component 1 is a pixelated X-ray detector means comprising a plurality of pixels arranged in an array that corresponds to the arrays of the connected single-photon detectors and counter circuits 26, which allows a spatial resolution of the sensed X-ray radiation 12.

The X-ray detector component 1 allows photon counting detection based on detecting X-ray radiation 12 by a direct conversion of X-ray photons to an electrical charge captured with the charge collecting electrodes 10 and provided to the CMOS read out circuit 24. During detection, field lines 28 extend from the top electrode 18 to the charge collecting electrodes 10, wherein the electrodes travel along the field lines 28 to the charge collecting electrodes 20. In this embodiment, the charge collecting electrodes 20 cover a wide area of the bottom side of the X-ray detector chip 22, which cause straight field lines 28 between the top electrode 18 and the charge collecting electrodes 10.

Figure 3:
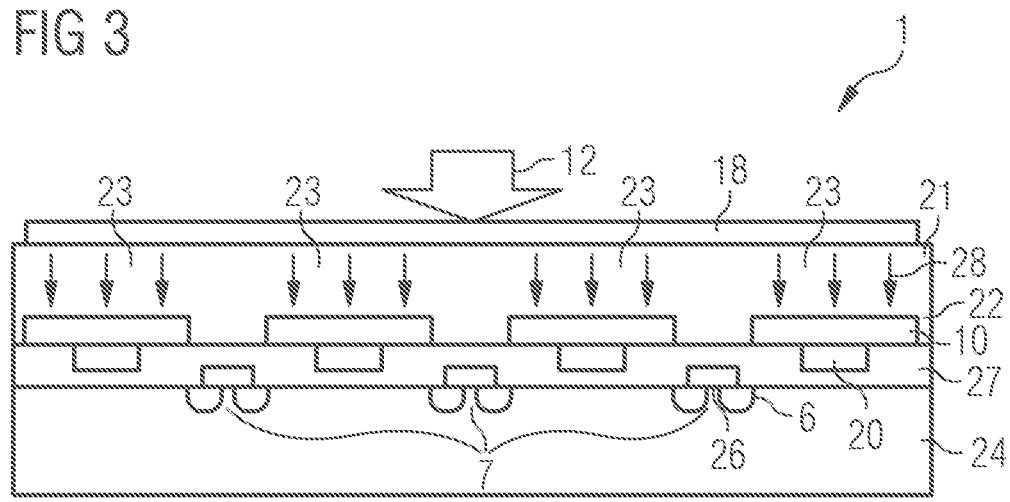
FIG. 3 shows an embodiment of an X-ray detector component.

A method for manufacturing the X-ray detector component 1 shown in FIG. 3 comprises providing an X-ray detector wafer that serves for providing the substrate for microelectronic devices built in and over the wafer. The thickness of the wafer may be between 0.1 mm and 1.0 mm. In a preferred embodiment the silicon wafer has a thickness of 725 mm and a diameter of 200 mm. The wafer includes a plurality of microelectronic devices including charge collecting electrodes 10 and being the basis of the X-ray detector chips 22. A CMOS read-out circuit wafer includes a plurality of microelectronic devices including connection electrodes 20 and being the basis of the CMOS read-out circuit chips 24. The X-ray detector wafer and the CMOS read-out circuit wafer are mechanically and electrically connected in such a manner that the charge collecting electrodes 10 and the connection electrodes 20 are electrically connected, thereby the microelectronic devices forming the X-ray detector chips 22 and the microelectronic devices forming the CMOS read-out circuit chips 24 are attached to each other. The connected X-ray detector wafer and CMOS read-out circuit wafer are separated into a plurality of X-ray detector components 1. They may be packed in a further step. Due to the separation step, sides of X-ray detector chips 22 and CMOS read-out circuit chips 24 have traces of separation.

Alternatively, the X-ray detector wafer and the CMOS read-out circuit wafer are separated into X-ray detector chips 22 and CMOS read-out circuit chips 24, respectively, before connecting them. In this method of manufacturing, the X-ray detector chips 22 and CMOS read-out circuit chips 24 are connected after the separating steps.

Figure 4:
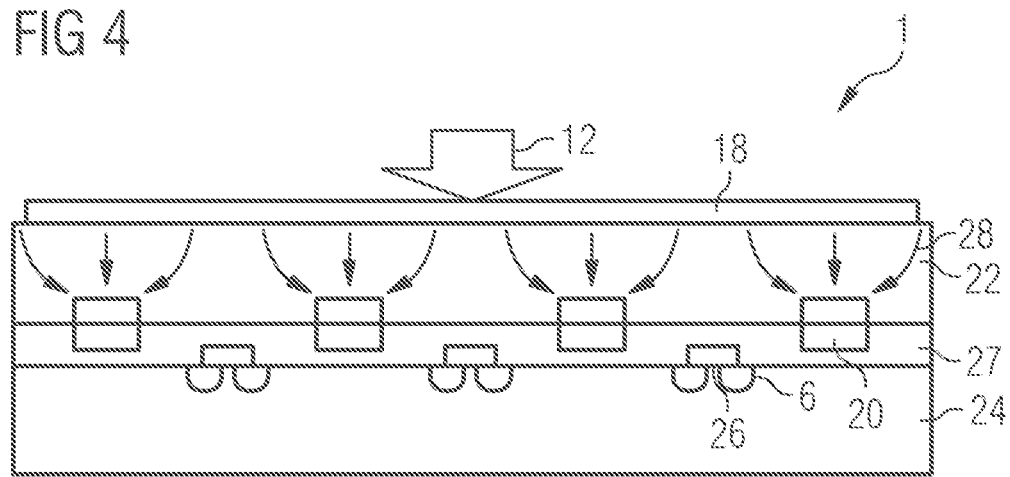
FIG. 4 shows a further embodiment of an X-ray detector component.

FIG. 4 shows a further embodiment of an X-ray detector component 1. Only differences to the embodiment shown in FIG. 3 are described in order to avoid repetition. Manufacturing may be performed as described above.

In this embodiment, the charge collecting electrodes 10 are smaller than in the aforementioned embodiment. Their surface area corresponds to the surface area of the connection electrodes 20. The size, thickness and form of the charge collecting electrodes 10 influence the field lines 28 and allow the electrons to be guided towards the charge collecting electrodes 10. The field lines 28 are curved, which shapes the path of the electrons and focuses the electrons to the charge collecting electrodes 10, thereby avoiding cross-talking effects. This effect is particularly important when dealing with thick absorbers in the X-ray detector chip 22, such as 725 μm silicon, in order to re-focus the electrons and not lose special resolution due to charge carrier spreading.

The width of the charge collecting electrodes 10 in this embodiment may be 3 to 4 μm. The width of the pixels may be 50 μm.

Figure 5:
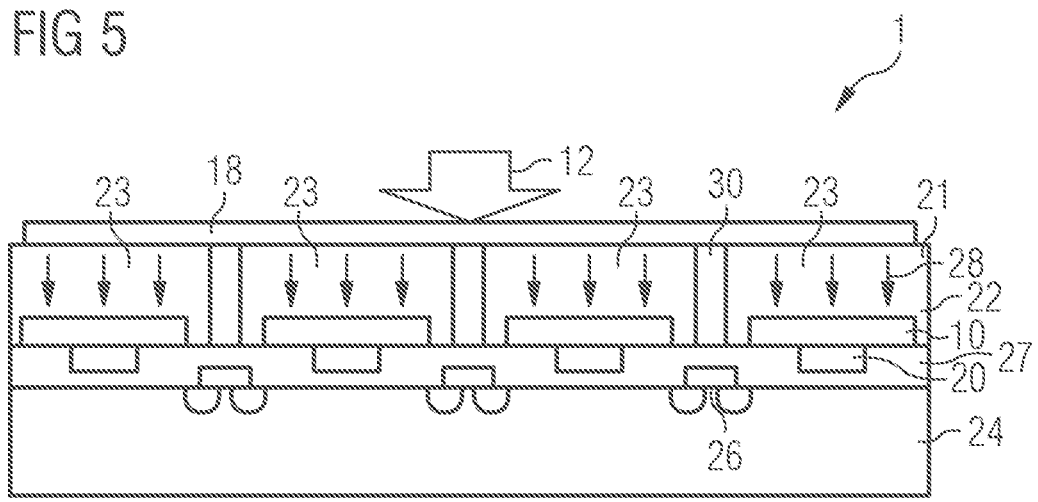
FIG. 5 shows a further embodiment of an X-ray detector component.

FIG. 5 shows a further embodiment of an X-ray detector component. Only differences to the embodiment shown in FIG. 3 are described in order to avoid repetition. Manufacturing may be performed as described above.

In this embodiment trenches 30 are arranged in the substrate 21, the trenches 30 extending between the charge collecting electrodes 20. The trenches 30 are formed in the substrate 21 to prevent cross-talk of neighboring pixels. The trenches 30 may be unfilled, e.g. ambient pressure or vacuum, or filled with a non-conducting material, preferably silicon dioxide. The trenches 30 have a preferred direction being orthogonal to the substrate surface. In this embodiment the trenches 30 extend from the top to the bottom of the substrate 21.

The trenches may be arranged in such a manner that each detector element 23 is surrounded by trenches 30, which may run between the rows and columns of a detector element array. Alternatively, the trenches extend between groups of detector elements 23.

The embodiments shown in FIG. 4 and FIG. 5 may be combined, i.e., curved electrical field lines 28 may be used to confine the charge carriers and, in addition, trenches 30 may be provided.

Figure 6:
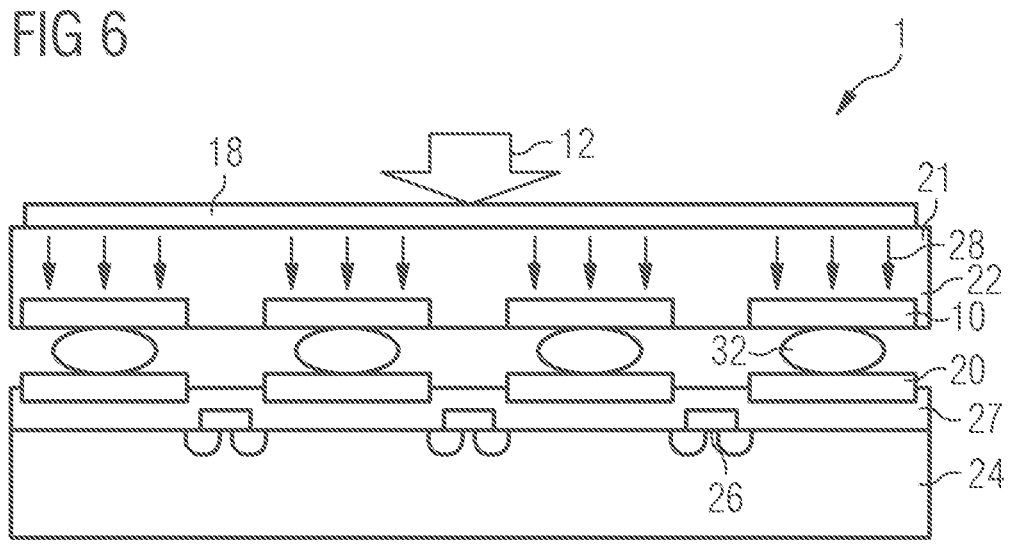
FIG. 6 shows a further embodiment of an X-ray detector component.

FIG. 6 shows a further embodiment of an X-ray detector component 1. Only differences to the embodiment shown in FIG. 3 are described in order to avoid repetition.

Contrary to hybrid bonds as interconnects, as shown in the previous embodiments of FIGS. 3 to 5, the X-ray detector chip 22 and the CMOS read-out chip 24 are connected by means of conventional interconnect technology, such as solder balls 32 or stud bumps, e.g. indium stud bumps. Manufacturing may be performed as described above. However, conventional interconnect technology is used for connecting the wafers.

As in the other embodiments, the sensor substrate 21 of the X-ray detector chip 22 is made from silicon and comprises at least one single-photon detector as an embodiment of a detector element. Typically, single photon detectors in silicon are referred to as single photon avalanche detectors (SPADs). The CMOS read-out circuit 24 comprises at least one counter connected to at least one single photon detector, thereby forming a photon counter detector.

Figure 7:
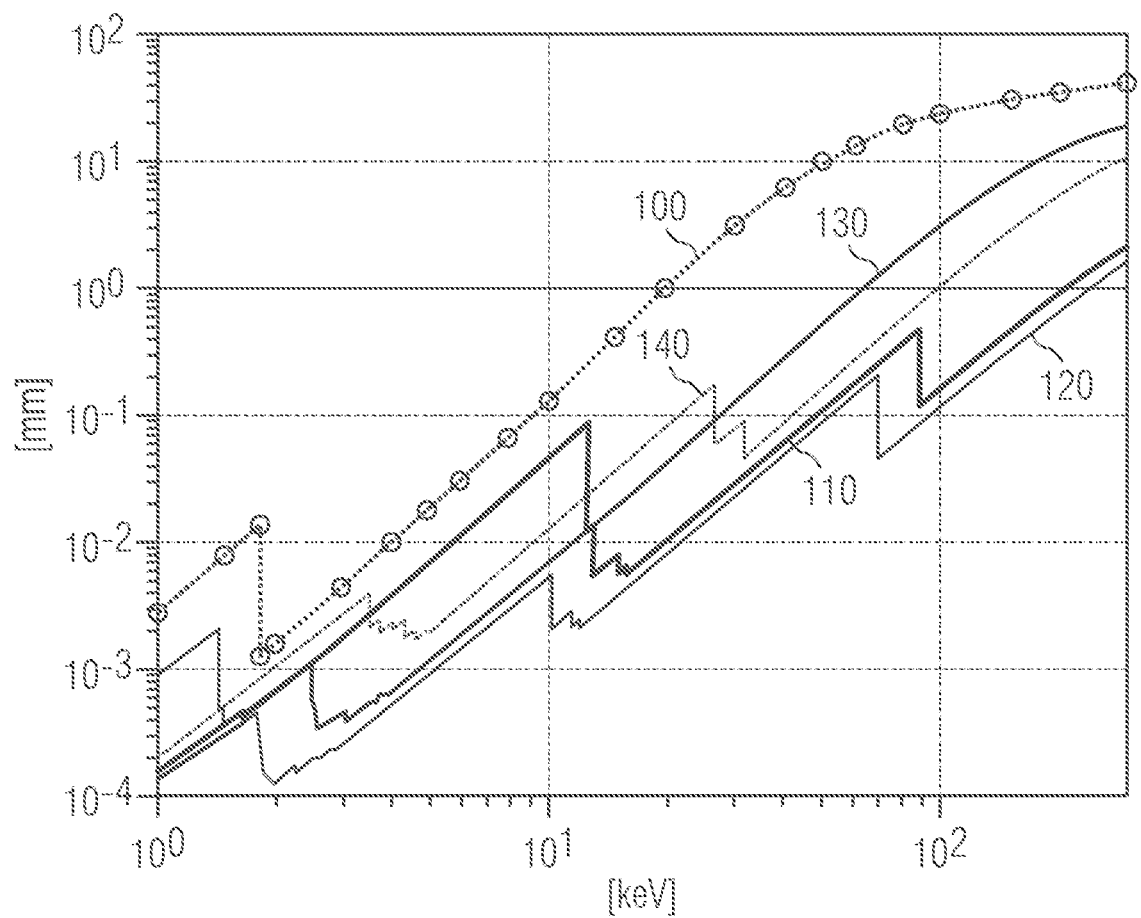
FIG. 7 shows a diagram illustrating absorption length versus energy.

FIG. 7 shows a diagram illustrating absorption length versus energy. The absorption length, also called absorption depth, in mm is shown over the X-ray energy in keV for different sensor substrate materials. Line 100 refers to silicon. Line 110 refers to lead. Line 120 refers to tungsten. Line 130 refers to selenium. Line 140 refers to cadmium telluride (CdTe).

For an X-ray energy of 30 keV as commonly used in mammography systems, the absorption length is about 20 to 30 μm for tungsten 120 and lead 110. For selenium 130 and silicon 100, the absorption length is 130 μm and 3 mm, respectively. Cadmium telluride 140 has an absorption length of 78 μm at 30 keV.

This observation might render silicon impractical for mammography applications; however, this is not the case as will be discussed below.

Figure 8:
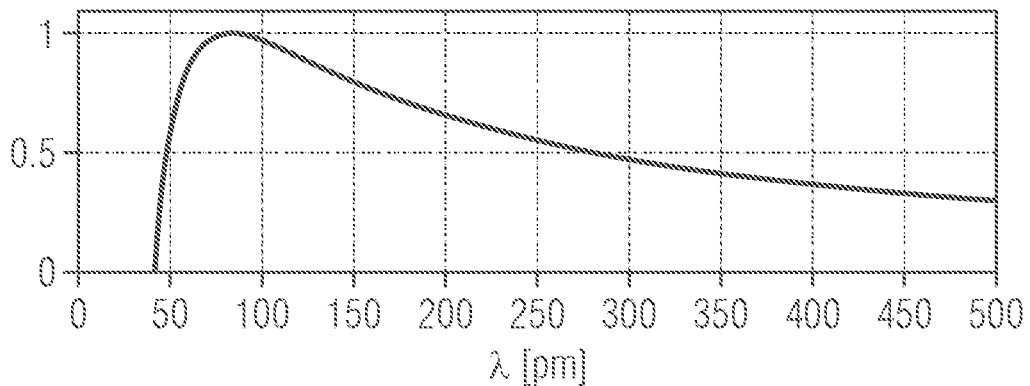
FIG. 8 shows an X-ray emission spectrum for a generic 30 keV X-ray source.

FIG. 8 shows an X-ray emission spectrum for a generic 30 keV X-ray source. The normalized X-ray intensity is shown over the wavelength λ in pm. The braking radiation was calculated with ab-initio principles, and is not dependent on the material of the anode. Note that, however, characteristic emission lines ($k_\alpha$, $k_\beta$, $l_\alpha$, etc.) are missing.

Then, the absorption efficiency was computed based on the characteristic, material dependent absorption length from FIG. 7. The resulting detective quantum efficiency (DQE) is shown in FIG. 9.

Figure 9:
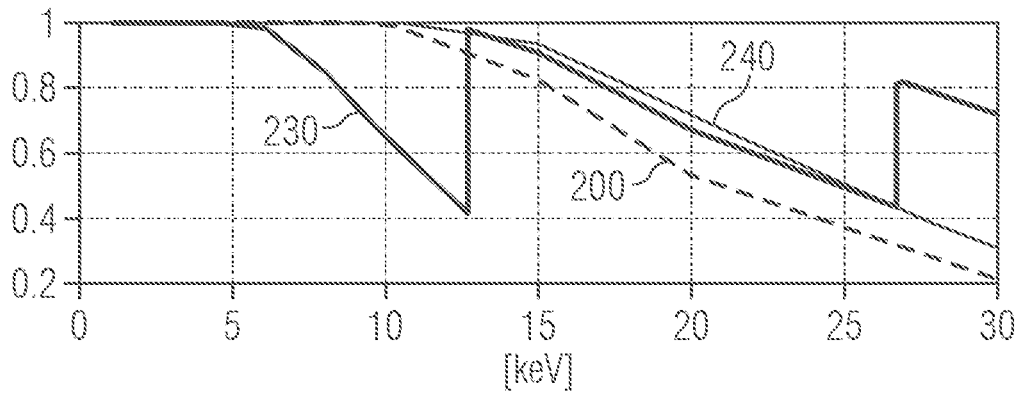
FIG. 9 shows an absorption efficiency for several types of chips.

FIG. 9 shows the absorption efficiency for a 725 μm thick silicon detector chip, a commonly used 100 μm thick selenium detector chip and a 100 μm CdTe detector chip. The normalized detective quantum efficiency is shown over the energy in keV. Line 200 relates to silicon. Line 230 relates to selenium. Line 240 relates to CdTe.

It is apparent that those materials are excellent absorbers for X-rays having low energies. However, beyond 15 keV the materials become transparent for X-ray radiation. Actually, the silicon chip outperforms a 100 μm thick selenium chip around 12 keV where selenium has a reduced absorption. Only a 100 μm thick cadmium telluride (CdTe) chip outperforms the silicon detector at the expense of being toxic and hazardous.

The overall unused X-ray intensities for both materials are in the same range but obviously dependent on the X-ray energy. Particularly around 10 to 13 keV, a 725 μm thick silicon chip is a better absorber than selenium.

In conclusion, the proposed silicon X-ray detector chip based on e.g., 725 μm thick fully depleted wafers has a similar X-ray absorption compared to conventional 100 μm thick amorphous selenium or CdTe chips.

Therefore, the proposed approach holds promise to allow for photon counting mammography systems at similar X-ray doses compared to conventional detectors.

Figure 10:
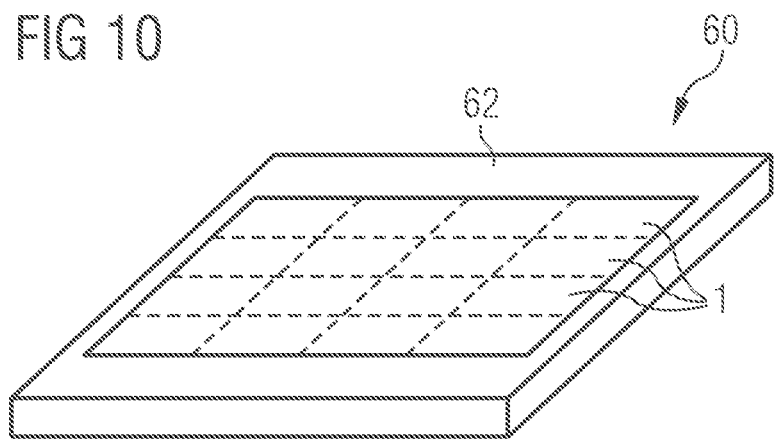
FIG. 10 shows an embodiment of an X-ray detection module comprising a plurality of X-ray detector components.

FIG. 10 shows an embodiment of X-ray detection module 60 comprising a multitude of X-ray detector components 1 arranged as an array in a frame 62. Such a flat panel detection module 60 may be placed in an image receptor of an imaging device. The imaging device may be an imaging medical device, e.g. for mammography or dental X-raying, or a screening device, e.g. for material error analysis or baggage scanning or packet scanning.

The scope of protection is not limited to the examples given herein above. The invention is embodied in each novel characteristic and each combination of characteristics, which particularly includes every combination of any features which are stated in the claims, even if this feature or this combination of features is not explicitly stated in the claims or in the examples.

The invention claimed is:

1. An X-ray detector component comprising:
   an X-ray detector chip made from a silicon substrate and comprising charge collecting electrodes; the X-ray detector chip being suitable for providing an X-ray-dependent current at the charge collecting electrodes;
   a CMOS read-out circuit chip comprising connection electrodes,
   wherein the X-ray detector chip and the CMOS read-out circuit chip are mechanically and electrically connected in such a manner that the charge collecting electrodes and the connection electrodes are electrically connected, and
   wherein the charge collecting electrodes and the connection electrodes are in direct mechanical and electrical contact.

2. The X-ray detector component according to claim 1, wherein the X-ray detector chip comprises a plurality of detectors.

3. The X-ray detector component according to claim 1, wherein the X-ray detector chip and the CMOS read-out circuit chip are connected by at least one hybrid bond.

4. The X-ray detector component according to claim 1, wherein the X-ray detector chip comprises a direct X-ray detector.

5. The X-ray detector component according to claim 1, wherein the X-ray detector chip comprises a single-photon detector.

6. The X-ray detector component according to claim 5, wherein the X-ray detector chip comprises a single-photon avalanche photodiode.

7. The X-ray detector component according to claim 1, wherein the charge collecting electrodes are formed in such a manner that field lines between a top electrode of the X-ray detector chip and the charge collecting electrodes are curved towards the charge collecting electrodes.

8. The X-ray detector component according to claim 1, wherein trenches extend between the charge collecting electrodes.

9. The X-ray detector component according to claim 8, wherein the trenches are filled with a non-conducting material.

10. The X-ray detector component according to claim 1, wherein the X-ray-detector chip is suitable to operate with X-ray photon energies equal or less than 100 keV.

11. The X-ray detector component according to claim 1, wherein the CMOS read-out circuit chip comprises a photon counter circuit.

12. The X-ray detector component according to claim 1, wherein the X-ray-detector chip is free of GaAs, CdTe, CdZnTe.

13. The X-ray detector component according to claim 1, wherein the X-ray-detector chip is configured to detect X-ray energies in the range between 25 keV and 35 keV.

14. The X-ray detector component according to claim 1, wherein the X-ray-detector chip comprises a top electrode arranged on a top side of the detector chip and the charge collecting electrodes are arranged on a bottom side of the detector chip.

15. The X-ray detector component according to claim 1, wherein the silicon substrate is depleted.

16. The X-ray detector component according to claim 1, wherein a back end of line of the CMOS read-out circuit chip faces the X-ray detector chip.

17. An X-ray detection module comprising a multitude of X-ray detector components according to claim 1.

18. An imaging device comprising an X-ray detection module according to claim 17, the imaging device being an imaging medical device or a screening device.

19. A method for manufacturing an X-ray detector component, the method comprising:
   providing an X-ray detector silicon wafer comprising a plurality of charge collecting electrodes;
   providing a CMOS read-out circuit wafer comprising a plurality of connection electrodes;
   mechanically and electrically connecting the X-ray detector wafer and the CMOS read-out circuit wafer in such a manner that the charge collecting electrodes and the connection electrodes are electrically connected;
   separating the X-ray detector wafer and CMOS read-out circuit wafer, which are connected, into a plurality of X-ray detector components,
   wherein the charge collecting electrodes and the connection electrodes are in direct mechanical and electrical contact.

20. An X-ray detector component comprising:
   an X-ray detector chip made from a silicon substrate and comprising charge collecting electrodes; the X-ray detector chip being suitable for providing an X-ray-dependent current at the charge collecting electrodes;
   a CMOS read-out circuit chip comprising connection electrodes,
   wherein the X-ray detector chip and the CMOS read-out circuit chip are mechanically and electrically connected in such a manner that the charge collecting electrodes and the connection electrodes are electrically connected,
   wherein the charge collecting electrodes and the connection electrodes are in direct mechanical and electrical contact and wherein the X-ray detector chip is free of CdZnTe.

* * * * *